US012648773B2

(12) United States Patent
Harper, Jr.

(10) Patent No.: US 12,648,773 B2
(45) Date of Patent: Jun. 9, 2026

(54) SAFETY SUTURE KIT AND METHOD OF USING

(71) Applicant: Uniformed Services University of the Health Sciences, Bethesda, MD (US)

(72) Inventor: Harvey Lee Harper, Jr., Bowie, MD (US)

(73) Assignee: Uniformed Services University of the Health Sciences, Bethesda, MD (US)

( * ) Notice: Subject to any disclaimer, the term of this patent is extended or adjusted under 35 U.S.C. 154(b) by 174 days.

(21) Appl. No.: 18/825,698

(22) Filed: Sep. 5, 2024

(65) Prior Publication Data

US 2025/0082323 A1     Mar. 13, 2025

Related U.S. Application Data

(60) Provisional application No. 63/537,040, filed on Sep. 7, 2023.

(51) Int. Cl.
*A61B 17/06*        (2006.01)
*A61B 17/04*        (2006.01)
(52) U.S. Cl.
CPC .... *A61B 17/06166* (2013.01); *A61B 17/0469* (2013.01); *A61B 17/0482* (2013.01)
(58) Field of Classification Search
CPC ... A61B 17/04; A61B 17/06; A61B 17/06166; A61B 17/0469; A61B 17/0482; A61B 17/0483
See application file for complete search history.

(56) References Cited

U.S. PATENT DOCUMENTS

| | | | |
|---|---|---|---|
| 3,333,846 A | 8/1967 | Glass et al. | |
| 4,789,340 A | 12/1988 | Zikria | |
| 6,048,351 A * | 4/2000 | Gordon .............. | A61B 17/0469 606/147 |
| 11,501,662 B2 | 11/2022 | Hofstetter et al. | |
| 2013/0211193 A1* | 8/2013 | Alexander ......... | A61B 17/3468 600/37 |
| 2015/0164501 A1* | 6/2015 | Hasan .............. | A61B 17/06166 606/145 |

OTHER PUBLICATIONS

Alcedo, "Suture Practice Kit," https://www.alcedohealth.com/pages/shop-suture-practice-kit?srsltid=AfmBOooldAqpm-MymaqppRN_I4EdTww4yjho4D0BV2ajFiZmngwQQxkY, downloaded from the internet Nov. 18, 2024.
Apprentice Doctor, "Suturing Practice Kit," https://www.amazon.com/Practice-Kit-Apprentice-Experienced-Right-Handed/, downloaded from the internet on Nov. 18, 2024.
Artagia Med Education Supplies, https://artagia.myshopify.com/, downloaded from the internet on Aug. 27, 2024.

(Continued)

*Primary Examiner* — Vi X Nguyen

(57)        ABSTRACT

A safety suture kit has layers of simulated tissue that move and close semi-independently of one another. Prefabricated incisions in the various tissue layers and prefabricated pathways coupled to the prefabricated incisions provide for a blunted needle to travel through the prefabricated incisions and pathways in order to move the tissue layers towards a closed position of a prefabricated incision. Elimination of sharps instrumentation such as needles, scissors and scalpel provides a safety suture kit suitable for suture simulation by users of all ages and abilities.

19 Claims, 11 Drawing Sheets

(56) References Cited

OTHER PUBLICATIONS

Hasbro, "Operation Game," https://en.wikipedia.org/wiki/Operation_ (game), downloaded from the internet Nov. 19, 2024.

Medarchitect, "Suture Practice Kit," https://mediarchitect.net/products/ medarchitect-suture-practice-kit-for-medical-students?srsltid= AfmBOoq5XDXbjjt_cdpUltYI3otPY63tlbgMOFLmjvp3pLI5iw_ O6X25, downloaded from the internet Nov. 18, 2024.

Medclimber, "New Generation Dental Suture Pad Practice Kit," https://cosmeticsurgerytips.com/product/dental-suture-practice-kit-for-students-and-dentists-4-types/, downloaded from the internet Nov. 19, 2024.

Medical Creations, "Suture Like a Surgeon Practice Kit," https:// medicalcreations.net/products/suture-practice-kit-1?srsltid= AfmBOopJqihXx6VDeqlizL-ziWa44HrB-CmQvUUMT8PtLPckhjE_- Vcr, downloaded from the internet on Nov. 18, 2024.

NeoProMedical, "complete Suture Kit," https://www.neopromedical. com/, downloaded from the internet Nov. 19, 2024.

USU News, "How this USU Student's Daughter Inspired His Surgery Invention," https://news.usuhs.edu/2023/02/how-this-usu-students-daughter-inspired.html, Feb. 2023.

WELLiSH, "Suture Practice Kit," https://www.amazon.com/Training-Medical-Practice-Include-Pre-Cut/dp/B098NRSC7Y, downloaded from the internet Nov. 18, 2024.

* cited by examiner

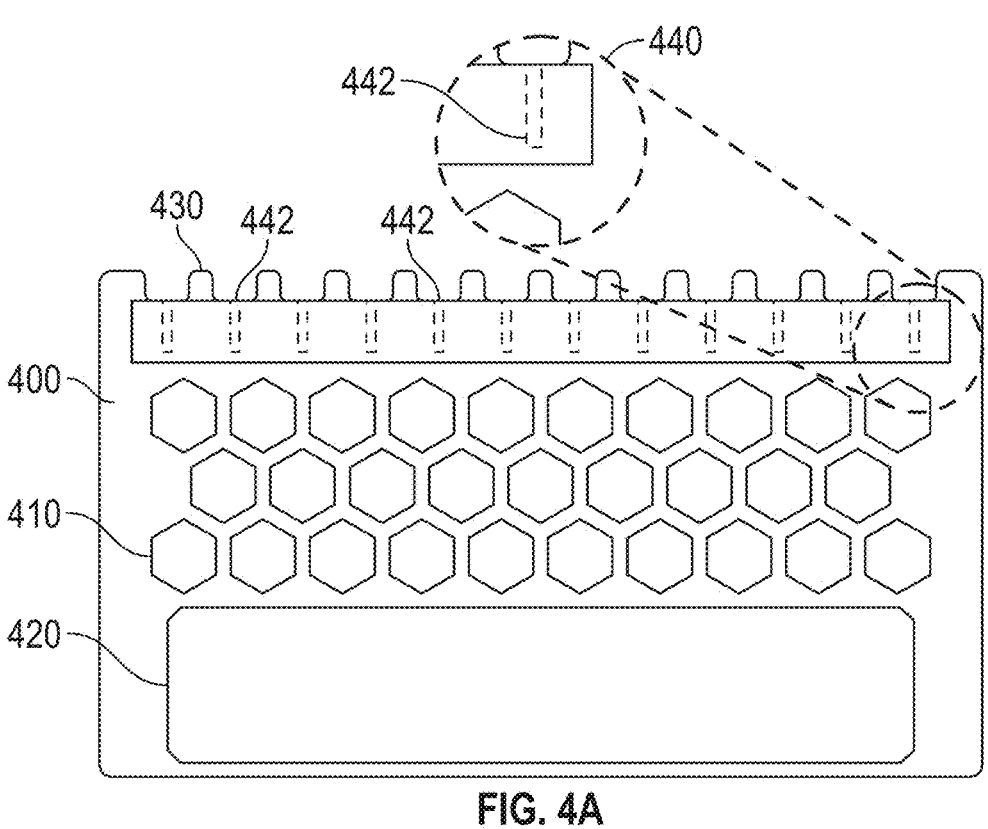
FIG. 4A
FIG. 4B
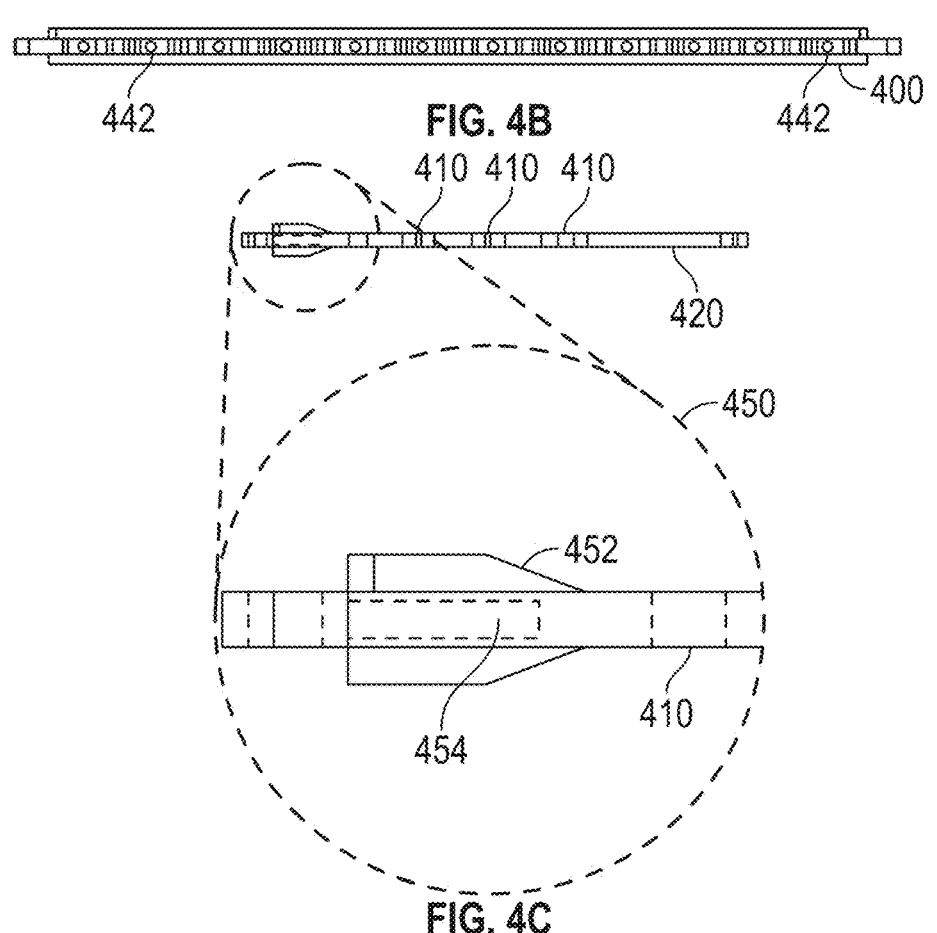
FIG. 4C

SAFETY SUTURE KIT AND METHOD OF USING

PRIORITY CLAIM

This application claims the benefit of provisional application Ser. No. 63/537,040 filed Sep. 7, 2023 and titled "Safety Suture Kit and Method of Using," the entire content of which is hereby incorporated by reference.

STATEMENT OF GOVERNMENT INTEREST

The invention described herein may be manufactured, used and licensed by or for the United States Government.

BACKGROUND

The present disclosure relates to medical training devices and techniques. More particularly, the present disclosure relates to suture training kits, devices and methods of training associated therewith.

Suture kits are necessary to help develop the fine motor skills and manual dexterity needed in a variety surgical specialties and subspecialties. A realistic suture kit presents significant safety concerns, particularly for young or inexperienced users seeking to improve their suturing technique. Of particular concern for these users is the risk of injuries from sharp instruments typically used, such as needles, scalpels and scissors.

As a result, suture kits are developed mainly for medical students and other health care providers. The few kits on the market suitable for the youngest users, such as those ages six and up, lack any suture capability. Even devices or kits labeled as "suture kits" for young users do not provide a realistic experience, often offering only plush toys or cards related to medical education with minimal hands-on opportunities.

Another common complaint of suture kits is the durability of the practice suture pad. Users report that a suture pad often rips when practicing deep stitches. Further, a suture pad will often also pull when practicing running subdermal stitches. Moreover, even if a stitch holds in an incision, then that specific incision is no longer a viable location to repeat the stitching technique a second time.

BRIEF DESCRIPTION OF THE DRAWINGS

FIGS. 4A-4C, provides an example layer scaffolding, before tissue is mounted thereon, in accordance with various embodiments of the present disclosure.

FIGS. 10A-10D illustrate prefabricated/predetermined pathways with prefabricated holes, in accordance with various embodiments of the present disclosure.

FIG. 11 illustrates an example prefabricated pathway with multiple options for prefabricated hole usage, in accordance with various embodiments of the present disclosure.

DETAILED DESCRIPTION

Figure 1:
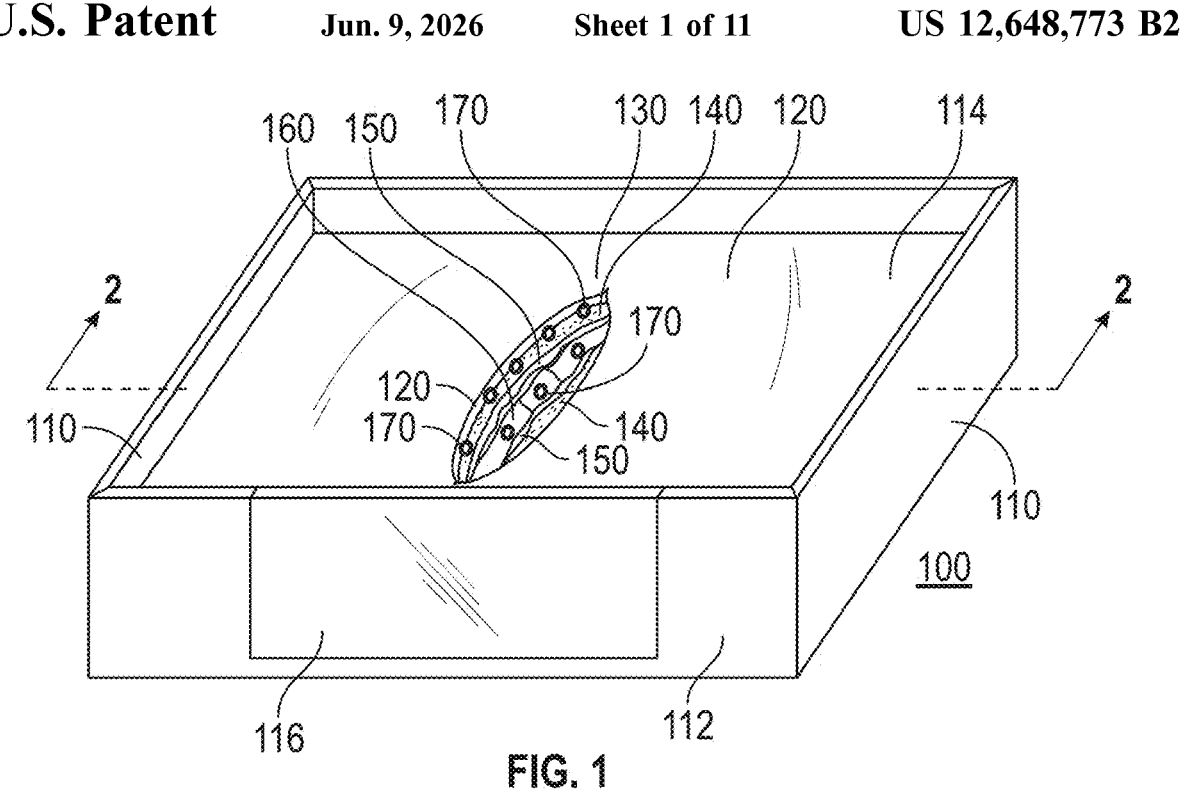
FIG. 1 depicts a safety suture kit, in accordance with various embodiments of the present disclosure.

Embodiments of the present disclosure will now be described with reference to the drawing figures, in which like reference numerals refer to like parts throughout.

The present safety suture kit generally relates to medical training devices, more particularly to simulation suture training kits, including materials for simulating the skin, sub-dermal tissue, deep-dermal tissue, adipose tissue, and muscle tissue, with layers of skin and tissue that move and close semi-independently of one another, prefabricated incisions in the various tissue layers, a prefabricated pathway for the needle to travel, reduction in sharps instrumentation with blunted needle for suturing to close pre-designed incisions in the simulated skin and tissue.

The innovative Safety Suture Kit described herein combines the realistic feel of surgery with the educational teaching of science, technology, engineering and math (STEM) and the childhood fun of the game "Operation" all in one kit. The "safety first" approach focuses on reducing the risk of sharp injuries to inexperienced or learning users and allows this product to be used by a broader age range than most suture kits on the market.

The safety suture kit is a simulation kit that significantly reduces the potential for sharp injury by eliminating the scalpel and suture scissors and replacing these tools with a blunted needle and, optionally, safety shears similar to those used in pre-k and kindergarten classrooms. The blunted needle eliminates the possibility of accidental sticks. A scalpel is not required due to the safety suture kit's prefabricated incisions and holes for sutures. This "safety first" approach allows the kit to be used by a broader age range of participants than suture kits on the market. For the very young, it's a great initial broad exposure to the interconnection of medicine and science. For children between 2nd and 5th grade, this simulation adds an additional layer of education to exposure beyond just diagrams and introduces the various layers of tissue involved in performing procedures like a laparotomy and represents the age where utilization helps to develop hand-eye coordination, especially for movements. For users ages 6th-12th, and beyond, the kit enhances the mechanics required in the operating room (O.R.) and helps familiarize them with the most commonly used suture techniques. For collegiate, pre-med, medical students, and other novice health professionals, the safety suture kit design provide a more realistic and holistic education while refining their skills to a level that they are ready to shadow or perform confidently on medical rounds.

As will be clear from the description that follows, a safety suture kit has a number of layers representative of tissue layers that are moveable and operable to be tensioned to a frame; one or more prefabricated incisions formed in the layers; and a number of prefabricated pathways and associated holes formed in the plurality of layers, each prefabricated pathway coupled to a prefabricated incision. Responsive to suture thread pushed into one or more holes of a prefabricated pathway of a prefabricated incision and guided through the prefabricated pathway under tension, one or more layers of the prefabricated pathway will move the prefabricated incision towards a closed position.

Figure 2:
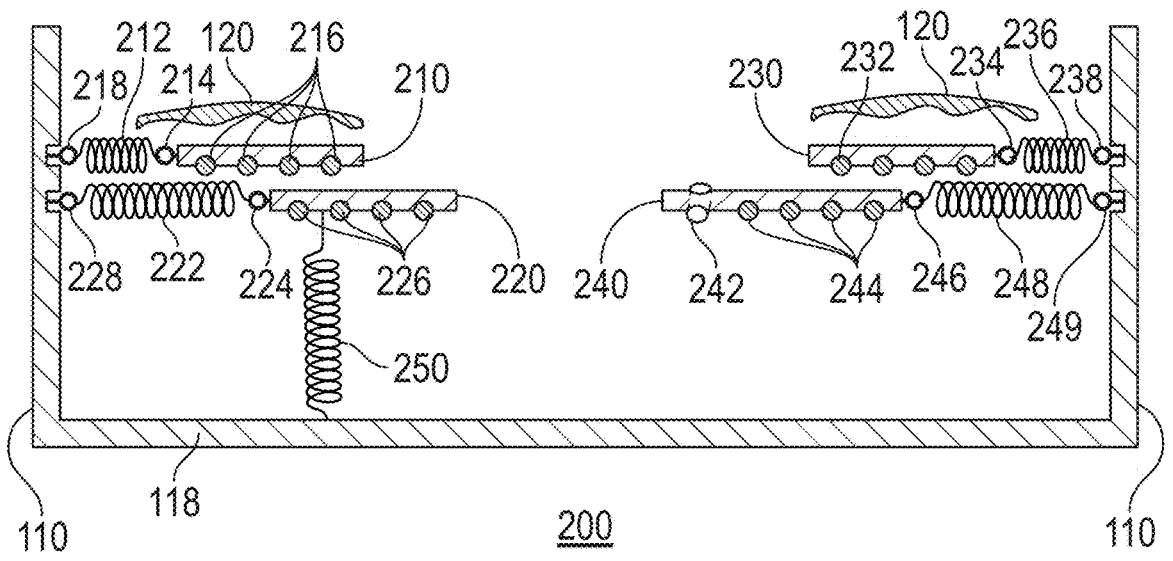
FIG. 2 shows a cross-sectional view of the safety suture kit of FIG. 1, in accordance with various embodiments of the present disclosure.

Referring now to FIG. 1, safety suture kit 100 is illustrated in accordance with various embodiments of the present disclosure; View 200 of FIG. 2 is a cross-sectional view of FIG. 1. The kit is formed in a frame or housing formed of side walls 110, front wall 112, back wall 114 and bottom 118. A window 116 is formed in front wall 112. Within the frame, a number of layers of tissues, including muscle, fat and various other layers are covered by a layer of skin or epidermis 120. A prefabricated incision 130 that is premade or preformed shows the various layers under the epidermis 120. For example, in the case of an abdominal wall, the layers are top skin or epidermis layer 120, Camper fascia (the fatty) layer 140 of superficial fatty layer of subcutaneous tissue, the Scarpa fascia (fibrous) layer 150 of deep membranous layer of subcutaneous tissue, and muscle layer 160 which may include external oblique, internal oblique, transversus abdominis, and rectus abdominis. Other, deeper layers of the anterior abdominal wall may include fascia transversalis, extra peritoneal fat and parietal peritoneum. These layers may or may not be included in prefabricated incision 130.

There are a number of prefabricate pathways formed in or connected to incision 130. There pathways are accessed via prefabricated openings 170 and the prefabricated pathways may be hidden or visible to the user as will be shown in other drawings. Any number of prefabricated incisions 130 may be formed within the layers and within other prefabricated incisions other or the same configurations of prefabricated pathways and openings of the pathways may be employed.

Window 116 permits a user to see the plurality of layers, the plurality of prefabricated pathways and associated holes, and the one or more fabricated incisions of the safety suture kit and indeed provides the user a sagittal view of one or more of the plurality of layers, the plurality of prefabricated pathway and associated holes, and the one or more fabricated incisions. As such, window 116 is preferably clear, translucent or another color or material that still permits the details of the structures resident in the incision to be readily and easily discerned.

In FIG. 2, the cross-sectional view 200 illustrates the layers 210, 220, 230, 240 are independently or semi-independently moveable with respect to one another through moving mechanisms 216, 226, 232 and 244, respectively. These moving mechanism may be wheels, slats or the like. The layers 210, 220, 230, 240 are tensioned to the frame formed by walls 110, 112, 114 and bottom 118 by one or more tensioning mechanisms that are coupled to the side walls 110 and bottom 118. Increased tension makes it harder to move a layer towards a closed position and tension may be adjusted by using or not using all of the tensioning mechanisms. In that regard, tensioning mechanisms may be replaceable and removable and any number of tensioning mechanisms may be adaptively used to adjust the amount of tension employed per layer. As an example of prefabricated pathways and holes, layer 240 has a prefabricated pathway 242 extending vertically through the layer with entry and exit holes as shown. The other layers may also have prefabricated pathways and holes extending therethrough as will be shown.

As shown in this particular embodiment, springs are used to provide spring-loaded tension each layers to the side walls 110 and also optionally may be used to tension a bottom layer, such as layers 220 and 240, to bottom surface 118 to provide more tension between the associated layer and the frame. An example of using a tensioning mechanism to tension a layer to the floor is shown by spring 250. Springs 212 and 222 are attached to the left side wall 110 via ring attachments 218, 228 and also are coupled to their respective layers 210 and 220 via ring attachments 214 and 224, respectively. Springs 236 and 248 are attached to the right side wall 110 via ring attachments 238, 249 and also are coupled to their respective layers 230 and 240 via ring attachments 234 and 246, respectively. Although other attachment mechanisms could be employed, the use of ring attachments allows the spring tensioning mechanisms to be easily and quickly changed out and replaced or simply removed.

While the tensioning mechanism may be devices other than springs, such as rubber bands, it has been found that individual springs provide spring-loaded tensioning mechanisms that increase durability and case of replacement or adjustment of tension based on user experience and strength. Spring loading may be more durable and provide better tension/stability than rubber bands, which tend to break. The tension of different springs, as well as rubber bands, may be adjustable. Moreover, both springs and rubber bands are replaceable and removable.

Figure 3:
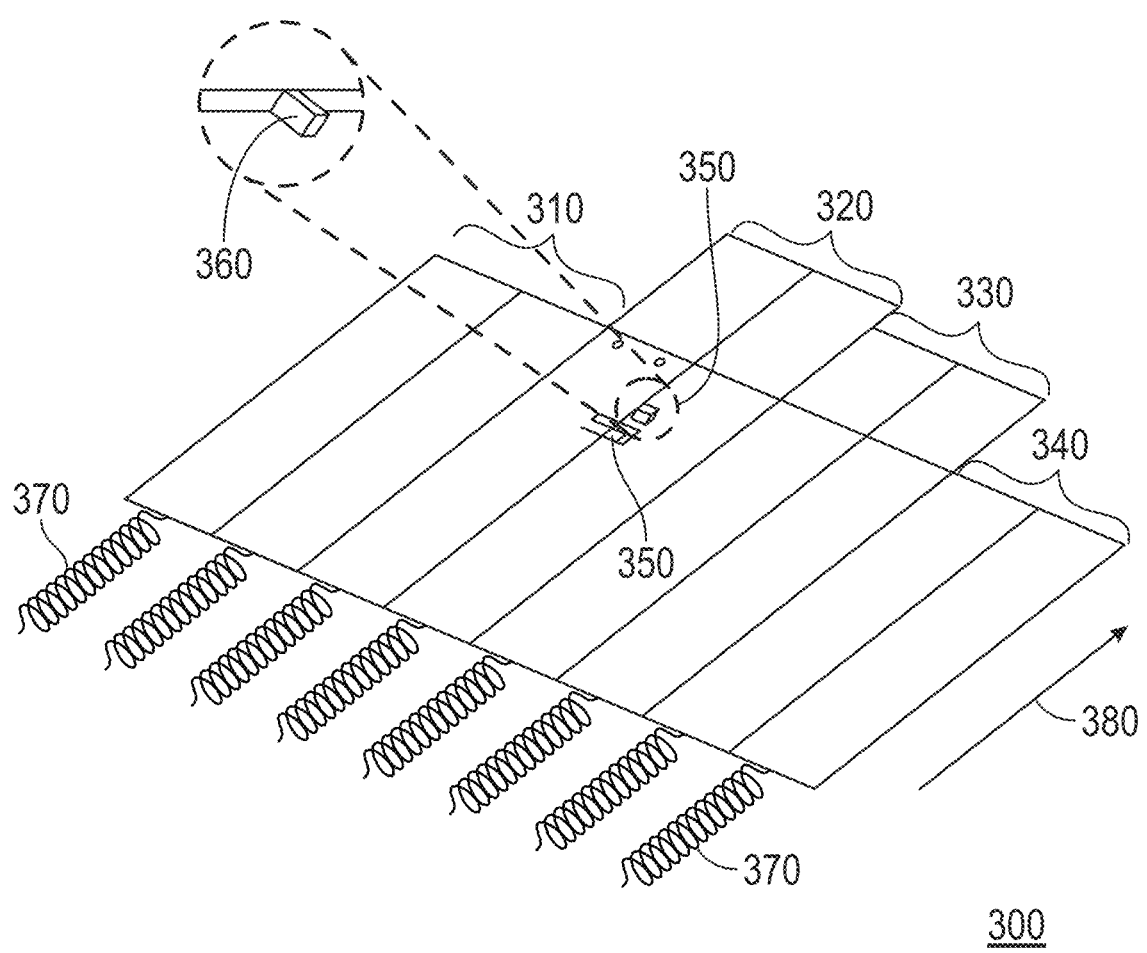
FIG. 3 provides a functional representation of an example embodiment of a layer, in accordance with various embodiments of the present disclosure.

Referring now to FIG. 3, a functional representation of an example embodiment of a layer 300 is shown. The safety suture kit may be adjusted to allow portions of a layer to move individually in a staggered fashion within that layer to make closure realistic. Each layer in this example may have 4-8 moving pieces that move sequentially in a staggered manner. In the drawing, four layer portions or slates 310, 320, 330, 340 are shown and because each of these portions is coupled to two springs 370, eight layer portions may be semi-independently moved. The ledges 350 underneath each slate catch on the adjacent slate after being pulled together, pulling the adjacent slate closer to closure without limiting the user's ability to throw the next suture. This ledge detail is shown in expanded view 360.

This feature is illustrated in the drawing by the relative movement of each of the layer portions in the direction of arrow 380. Movement of the layer 300 results in first layer slate 320 moving first in direction 380. When the latch 350 of first layer slate 320 catches adjacent, second layer slate 330, this causes second layer slate 330 to also start moving in direction 380 together with first layer slate 320. This may be followed in turn by movement of slates 310 and 340 as further ledges under first and second layer slates 320, 330 catch on slates 310 and 340.

Adjusting the tension provided by spring-loaded tensioning mechanisms spring 370, e.g. springs, allows some layer portions or slates to be easier or harder to independently or semi-independently move. For example, layer 320 may be coupled to weaker springs than those attached to layer 330; that makes it easier to be moved in the direction of arrow 380 than layer 330. Similarly, layer 330 may have weaker springs attached to it than those attached to layers 310, 340, allowing a user to be able to move layer 330 in the direction of arrow 380 than layers 310, 340. In such an example, the user would find it progressively harder to move the layer 300 in the direction 380, perhaps simulating suturing through various layers.

This semi-independent movement of layer slates works in both directions, i.e. towards closure of an incision in direction 380 or in the reverse direction to open an incision. In this manner, it can be seen that layers, such as layers, 210, 220, 230 and 240 of the safety suture kit may include one or more slates that move semi-independently in a first progression in a first direction and in a second progression that is opposite of the first progression in a second direction. Adjacent layer portions or slates are coupled to each other by a corresponding latch.

Referring now to FIGS. 4A-4C, an example layer scaffolding or board 400 used for an example layer, before tissue is mounted thereon, is shown. The surface of scaffolding 400 is punctuated by a number of holes 410 that can accommodate placement of a pre-fabricated pathway and a large window 420, shown in FIG. 4A. While the holes or openings 410 in scaffolding 400 are shown as forming a honeycomb, other shapes for openings 410 may be employed. At one end of the scaffolding are protrusions or nubs 430 as well as structures 442 shown in enlargement 440. FIG. 4B is a cross-sectional view of scaffolding 400. FIG. 4C illustrates a cross-sectional view of the side of the scaffolding in which the openings 410 and an example lip structure 452, 454 is shown in enlargement 450.

Figure 5:
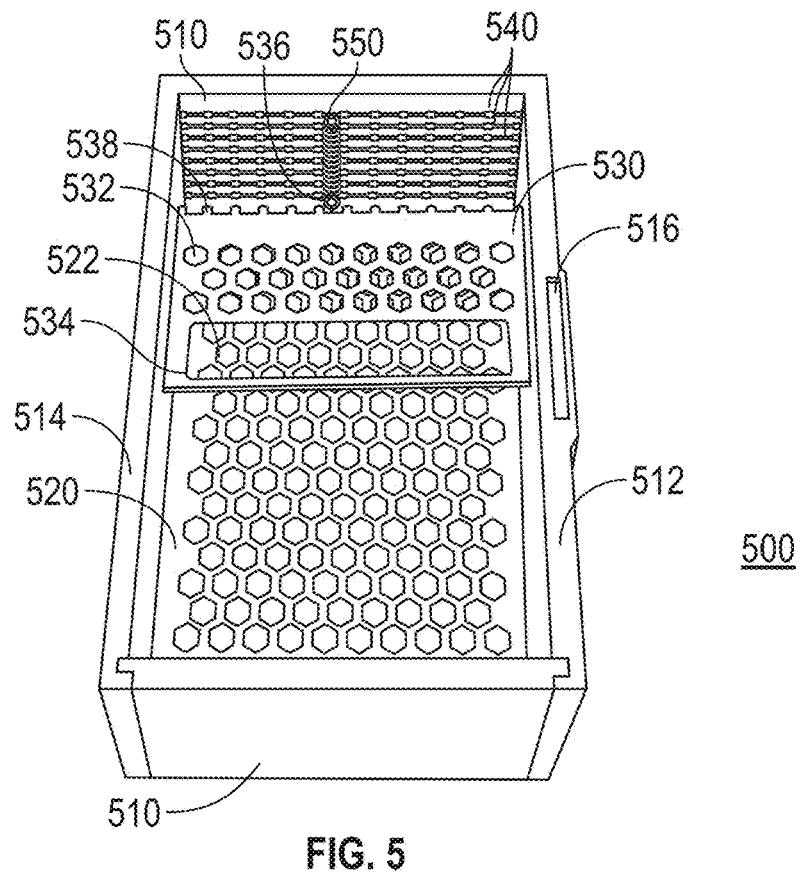
FIGS. 5 and 6 illustrate placement of layer scaffolding placed within a frame or housing of a safety suture kit, in accordance with various embodiments of the present disclosure.
Figure 6:
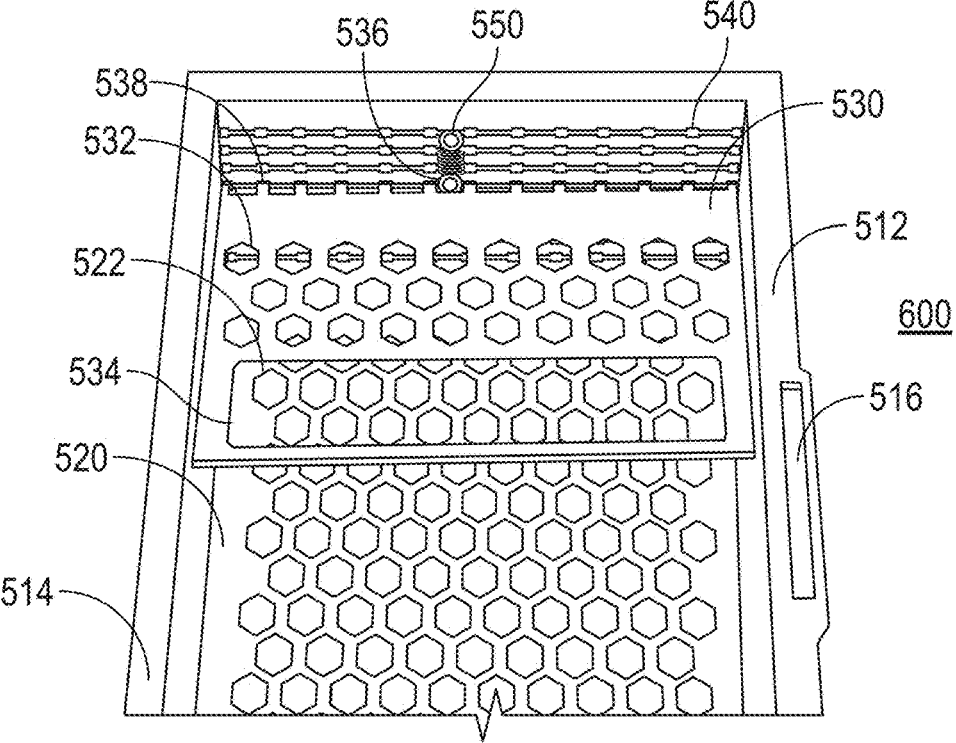

Referring now to FIGS. 5 and 6, examples of placement of the scaffolding 400 placed within a frame or housing is illustrated. In FIG. 5, safety suture kit 500 shows a frame formed of side walls 510, front wall 512 with observation window 516, back wall 514 and bottom 520. Both scaffolding layer 530 and base 520 have holes or openings 532, 522, respectively, that form honeycomb patterns of like shape and size, although this is not required so long as there are openings that accommodate the placement of pre-fabricated pathways. Layer scaffolding 530 rest within one of the slots or ledges 540 formed around the perimeter of one or more of the walls 510, 512, 514, which permit scaffolding 520 to move as it is pulled towards a closed position during a simulated suturing exercise. One or more ring attachments 550 on the side wall 510, such as on each ledge 540, and corresponding ring attachments 536 on the end of scaffolding 530 adjacent to a series of protrusions or nubs 538 provide for ready attachment of tensioning mechanisms like springs to be used to couple under tension the scaffolding 530 to the side wall(s) 510 of the frame of the safety suture kit.

Figure 7:
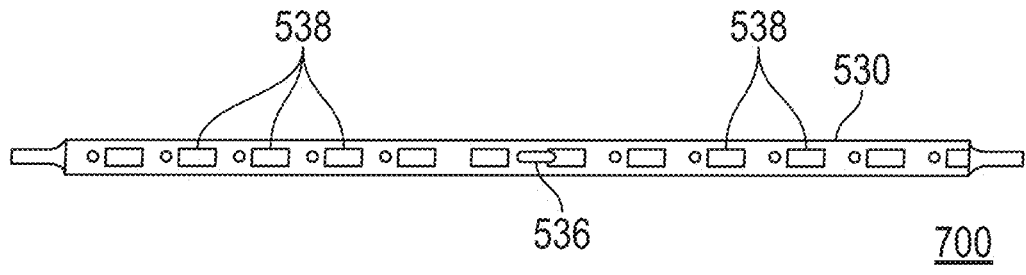
FIG. 7 illustrates the end edge of layer scaffolding, in accordance with various embodiments of the present disclosure.

The scaffolding layer 530 is shown with the opening 534 pulled towards the center of frame 500 in a "close" position that may be used to close a pre-fabricated incision formed by a multiple of layers 530 within kit 500. Pulling against the tension mechanism of springs placed between the side wall of the enclosure of the end of the scaffolding layer is required to pull the opening towards the center. Contrast this with kit 600 of FIG. 6 in which the layer scaffolding 530 is moved back into an open position and is under less tension. FIG. 7 illustrates scaffolding 700 in which the end edge of layer scaffolding 530 with protrusions or nubs 538 and ring attachment 536.

Figure 8:
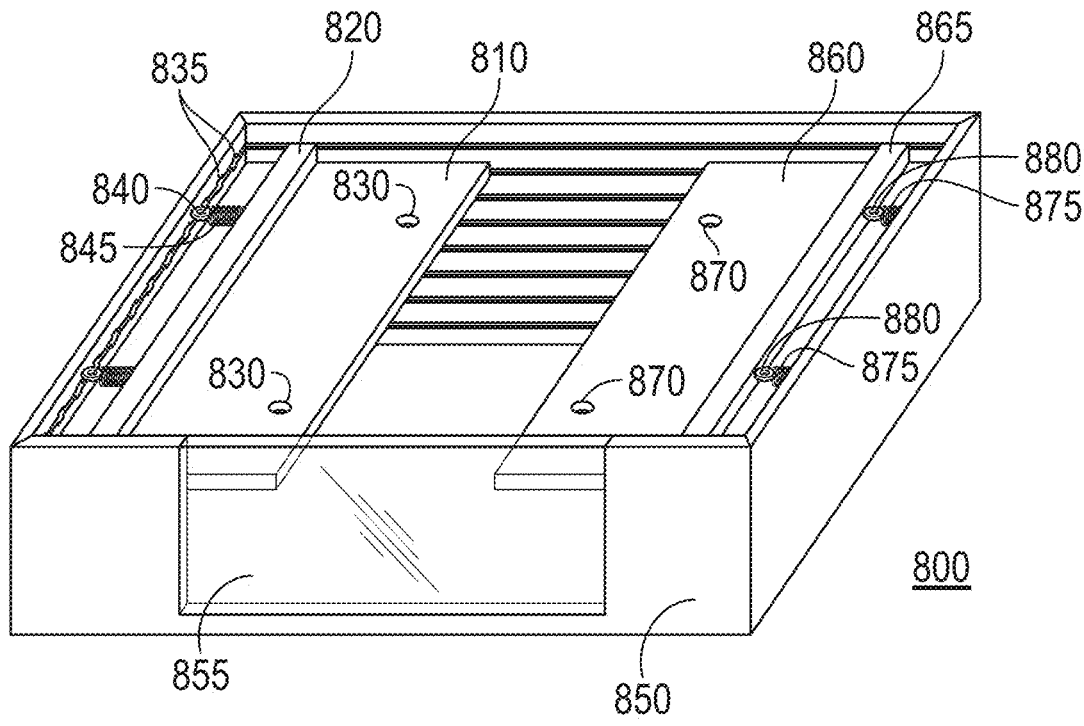
FIG. 8 depicts a safety suture kit with layer scaffolding and tensioning means within a frame, in accordance with various embodiments of the present disclosure.
Figure 9:
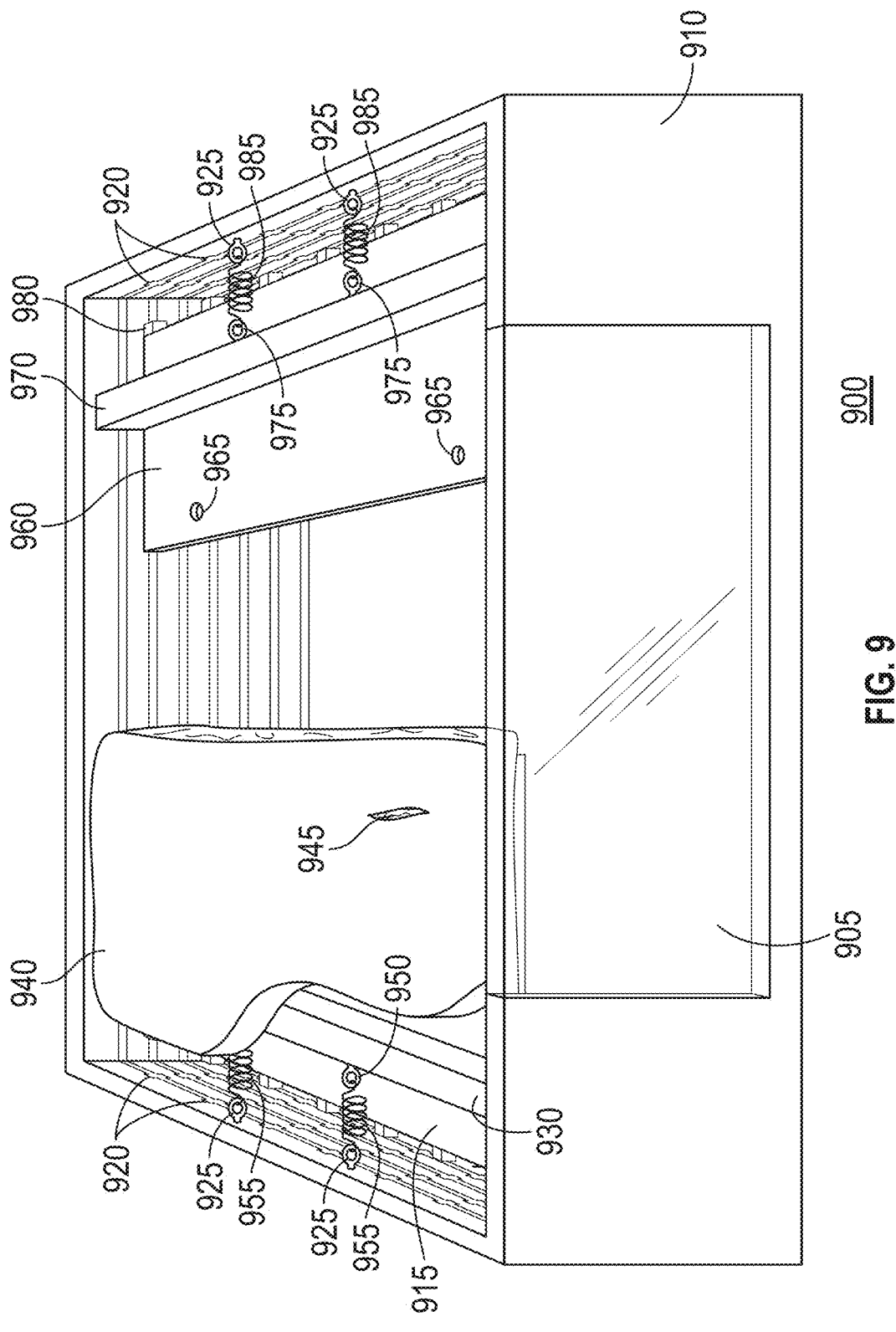
FIG. 9 illustrates a safety suture kit with a multilayer arrangement beneath epidermis and within a frame, in accordance with various embodiments of the present disclosure.

Referring now to FIGS. 8 and 9, safety suture kits are shown. FIG. 8 depicts a safety suture kit with layer scaffolding and tensioning means within a frame, before tissue material is added to the layers, while FIG. 9 shows a safety suture kit with a multilayer arrangement beneath epidermis and within a frame.

Referring now to FIG. 8, safety suture kit 800 has a frame 850 that has a window 855 for viewing the layer scaffolding within the frame. At this stage of manufacture, before tissue material is added, scaffolding layer portions 810, 820 on the left and 860, 865 on the right can be seen. As previously discussed, these scaffolding layer portions can move together or in stages as slates within slots or ledges 835 of the frame 850. As shown in FIG. 9, these scaffolding layer portions are covered with the tissue into which one or more pre-cannulated pathways may be arranged in an incision within the tissue layers. Holes 830 within scaffolding layer portion 810 and holes 870 within scaffolding layer portion 860 may accommodate such prefabricated pathways and/or form the opening holes at the ends of such pathways. Scaffolding layers 810, 820 are tensioned to the sidewall by tensioning mechanisms, shown here as springs 845 removably affixed to the left side wall via ring attachments 840. On the right side, scaffolding layers 860, 865 are tensioned to the sidewall by tensioning mechanisms, shown here as springs 875 removably affixed to the right side wall via ring attachments 880. Although not visible, one or more of the scaffolding layers 810, 820, 860, 865 may additionally be tensioned to the base 865 by one or more tensioning springs attached to the underside of the layers.

In safety suture kit 900 of FIG. 9, an example is shown in which tissue layers and an incision 945 form therein are shown over the left scaffolding layer portion(s) 915, 930 that are free to move or glide within slots 920 of the frame 910, together or as slates whose movement are staggered. An observation window 905 within frame 910 allows a user to observe incisions and layers formed therein. The top tissue layer is the epidermis 940. On the left, the left scaffolding layer portion(s) 915, 930 are tensioned to the left wall of the frame by tensioning springs 955 via a ring attachment 950 of the scaffolding layer portion(s) 930 and ring attachments 925 of the left wall. On the right side, the right scaffolding layer portions 960, 970, is unadorned by tissue material are free to move or glide within slots 920 of the frame. Right scaffolding layer portion 960 has end protrusions or nubs 980 as shown. Right scaffolding layer portion 970 has ring attachments 975 and may be tensioned to the right side wall by tensioning springs 985 removably attached to ring attachments 975 and corresponding ring attachments 925 affixed to the right wall. Holes 965 within scaffolding layer portion 960 may accommodate prefabricated pathways and/or form the opening holes at the ends of such pathways within an incision in tissue layers to be placed on scaffolding layer portions 960, 970.

Figures 10A, 10B, 10C, 10D, 11:
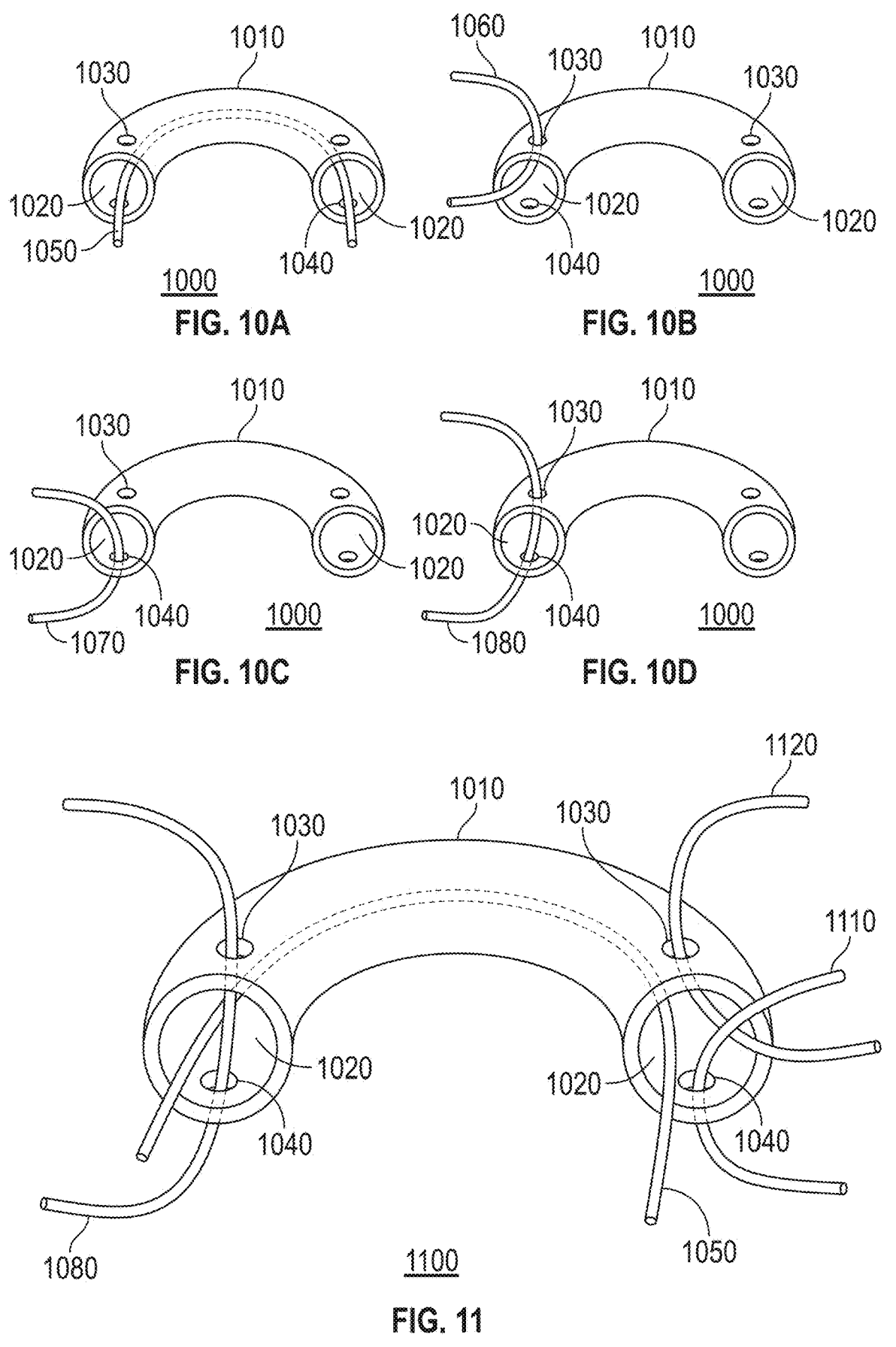

Referring now to FIGS. 10A-10D, a series of examples 1000 of prefabricated/predetermined pathways 1010 with prefabricated holes are shown. A variety of different configurations of prefabricated pathways 1000 and arrangement of holes therein may be employed, depending on the desired suture method and holes chosen. These options in prefabricated pathways 1010 include hole openings 1020 at either end of the pathway, holes 1030 on a top surface of pathway 1010, holes 1040 in a bottom surface of pathway 1010; holes could additionally be placed in the sides of pathway 1010. In FIG. 10A, an example thread 1050 is threaded through pathway 1010 in a horizontal orientation from opening holes 1020 to 1020 as shown. FIGS. 10B-10D illustrate orientations of the threads based upon more vertical throws of the blunted suture needle through the same prefabricated holes. In FIG. 10B, thread 1060 is threaded through an opening hole 1020 and a top hole 1030. FIG. 10C illustrates thread 1070 threaded through a bottom hole 1040 and opening hole 1020. FIG. 10D illustrates example thread 1080 thread in a more vertical direction through top and bottom holes 1030, 1040, respectively. In example 1100 of FIG. 11, it can be seen that a single prefabricated pathway 1010 may be used and reused by a number of threads in various configurations. In addition to again showing threads 1050 and 1080 from FIGS. 10A and 10D, example threads 1110 and 1120 illustrates generally vertical orientations of the respective threads.

Figure 12:
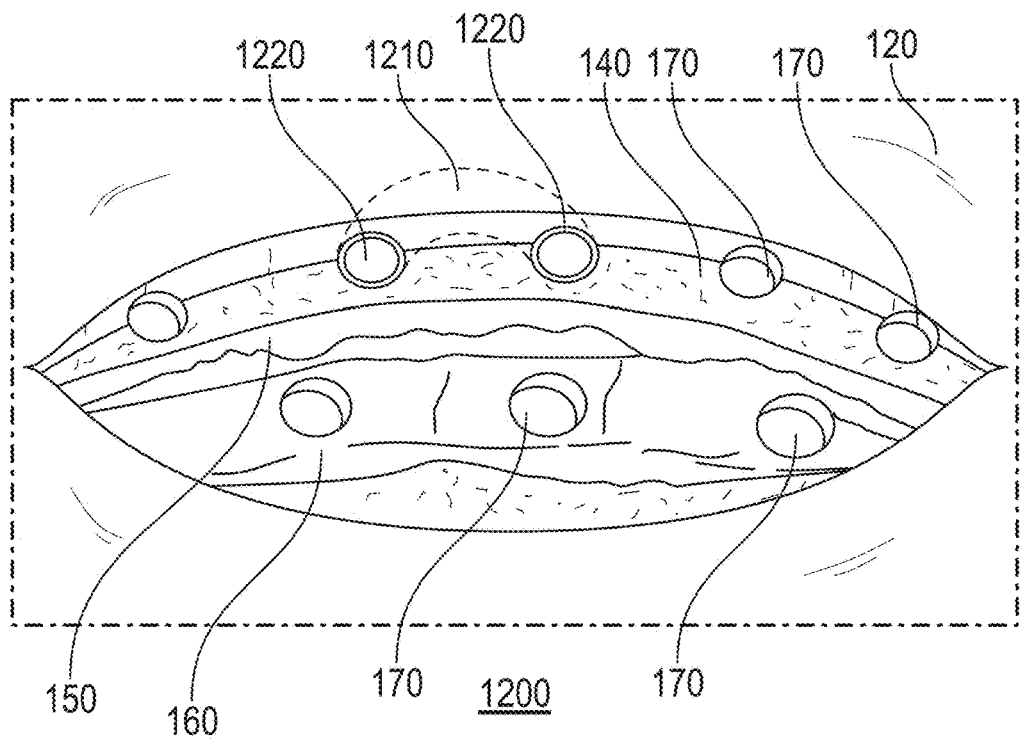
FIG. 12 shows an example incision with prefabricated pathways and prefabricated holes connected thereto, in accordance with various embodiments of the present disclosure.

In FIG. 12 an example incision 1200 is shown with the prefabricated holes 170 previously shown in FIG. 1. Also shown is prefabricated pathway 1210 with end openings 1220. Other prefabricated openings, such as top, bottom and side, could be part of pathway 1210. Additionally, the orientation of unshown pathways between prefabricated holes 170 could allow for many different prefabricated pathways of horizontal, vertical, or sideways orientations.

Figure 13:
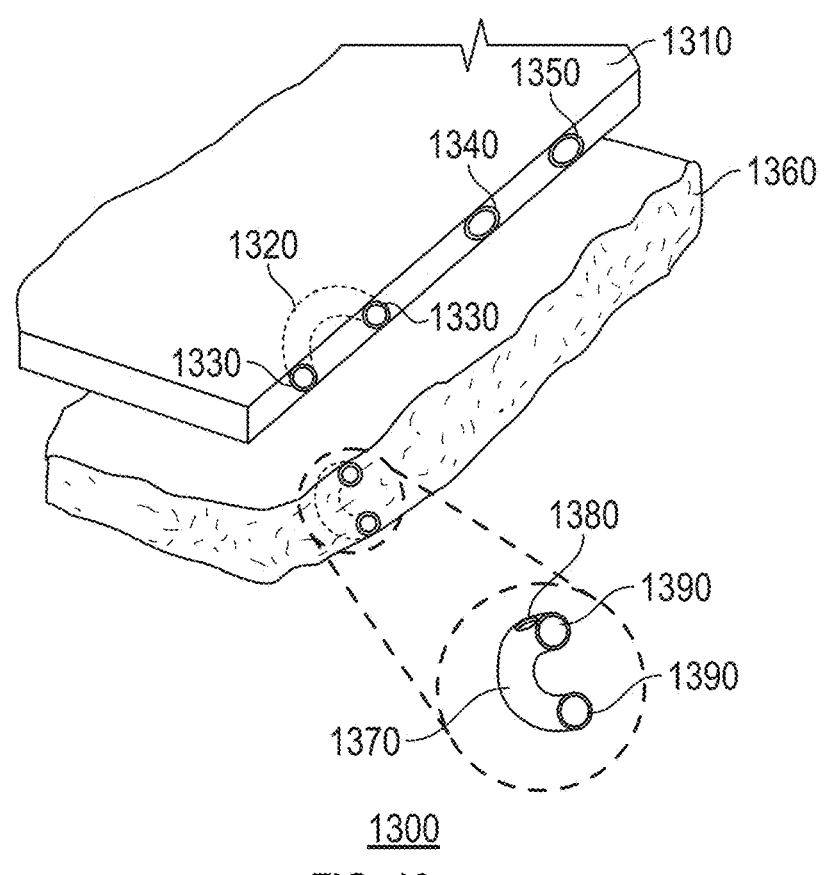
FIG. 13 illustrates different orientations of prefabricated pathways with various configurations of prefabricated holes, in accordance with various embodiments of the present disclosure.

An example 1300 of two layers 1310 and 1360 in FIG. 13 illustrates the different orientations of prefabricated pathways with various configurations of prefabricated holes. Top layer 1310 shows four prefabricated holes 1330, 1340, 1350 with two end holes 1330 of prefabricated pathway 1320 having horizontal orientation. In lower layer 1360, prefabricated pathway 1370 is arranged in a vertical orientation with three prefabricated holes: side hole 1380 and end holes 1390.

Figure 14:
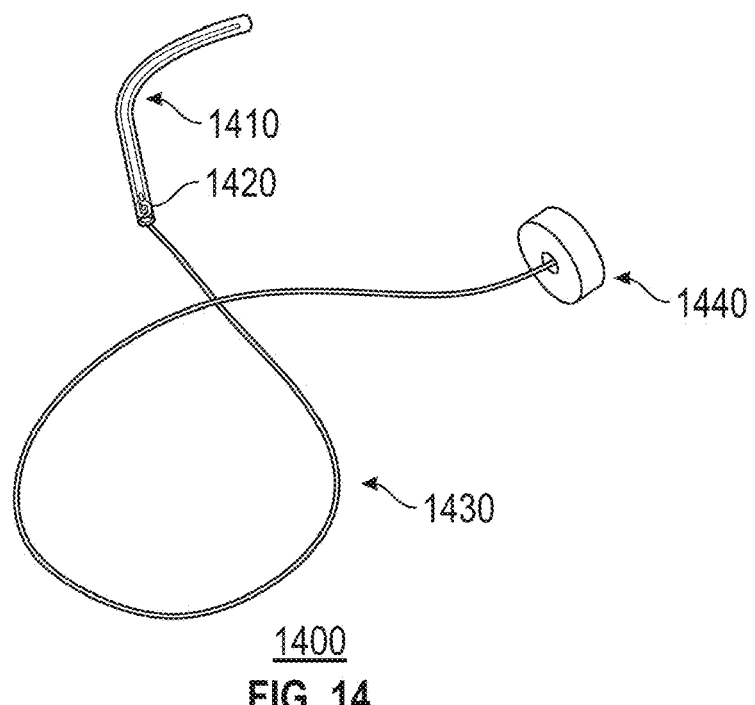
FIG. 14 illustrates an example blunted needle-suture thread-anchor assembly of a safety suture kit, in accordance with various embodiments of the present disclosure.

Turning to the blunted needle used with the safety suture kit, FIG. 14 illustrates an example blunted needle-suture thread-anchor assembly 1400 of a thread or suture 1430 attached to a blunted needle 1410 within an optional protective cover 1420, such as a plastic cannulated cover, at one end and an anchor 1440 at the other, distal end. In some embodiments, the anchor 1440 is used to allow users who are unable to make a knot to still be able to perform running suture techniques as will be described.

Figure 15A:
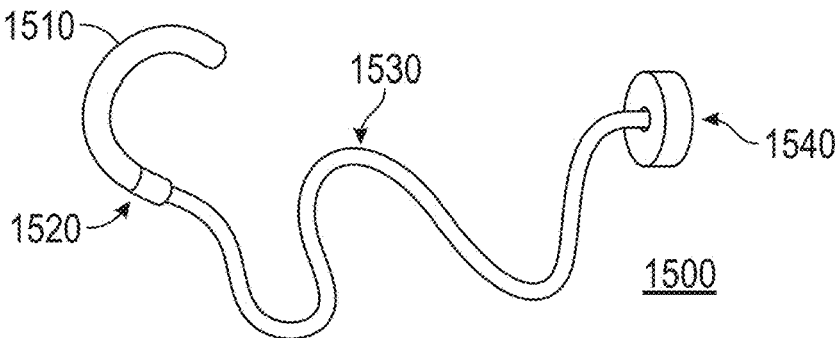
FIGS. 15A and 15B illustrate an example blunted needle-suture thread-anchor assembly of a safety suture kit, in accordance with various embodiments of the present disclosure.
Figure 15B:
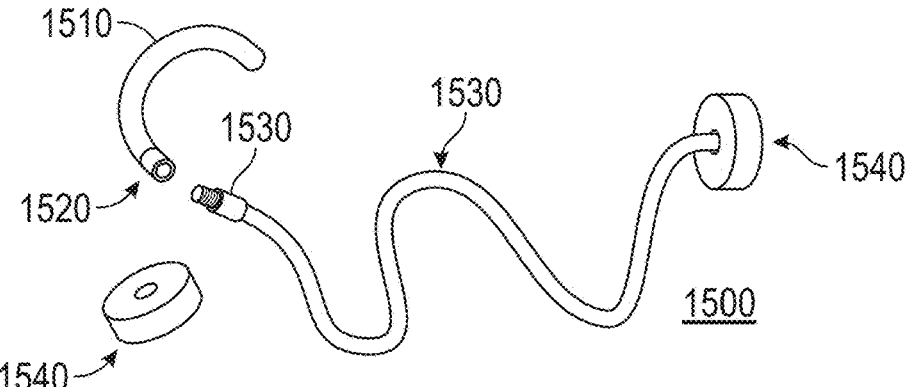

FIGS. 15A and 15B illustrate an example blunted needle-suture thread-anchor assembly 1500 of a safety suture kit, in which a detachable needle is shown. The suture or thread is coupled to the blunted needle 1510 at a point of articulation 1520. The screw end 1530 of the suture string 1530 can be screwed into a second anchor 1540 to hold tension once the user has come to a stopping point.

Driving the blunted needle through the prefabricated incisions in the skin like the top layer and prefabricated cannula pathways coursing through the deeper layers was easier for users with previous suture experience than users without experience. The blunted needles encased in nasal cannula tubing created a blunted end and surface that moved more smoothly through prefabricated skin incisions and cannula pathways within the deeper layers compared to earlier designs of suture needles and thread. The needle anchor, for those new to suturing, allowed users to exhibit vast improvement by practice and better mechanics using the needle driver and pick-ups was obtained. Multiple trials found that springs appropriately sized provided appropriate tension to make closing the incision more realistic as well as provided enough tension to prevent the incision from coming together all at once or with inadequate pressure.

Figure 16:
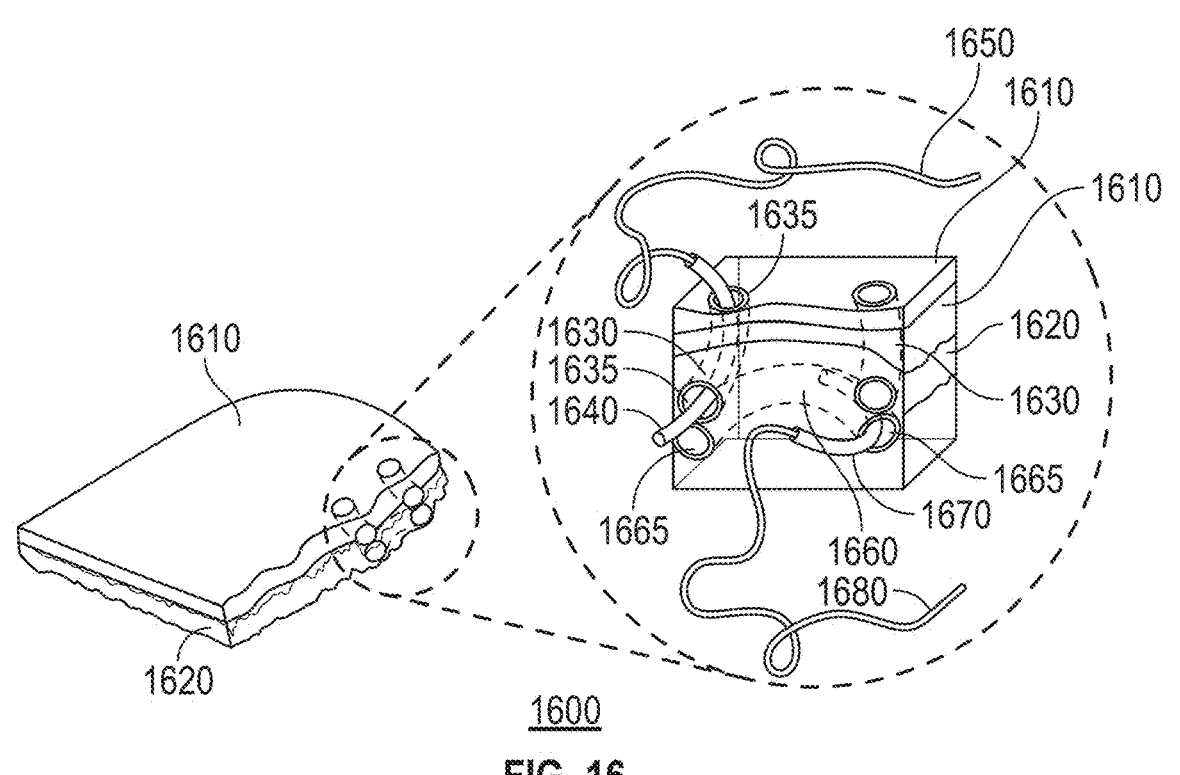
FIGS. 16, 17 and 18 illustrate examples of sutures of various orientations and suture types, in accordance with various embodiments of the present disclosure.
Figure 17:
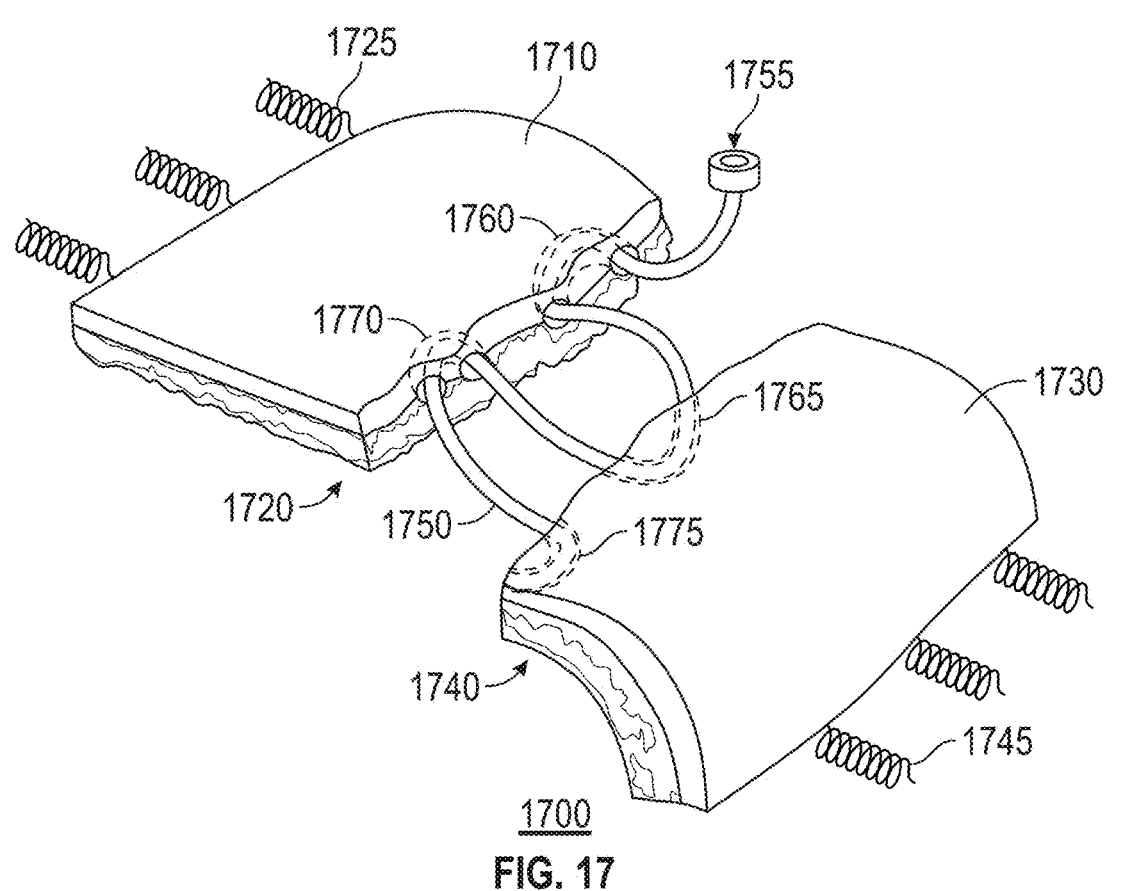
Figure 18:
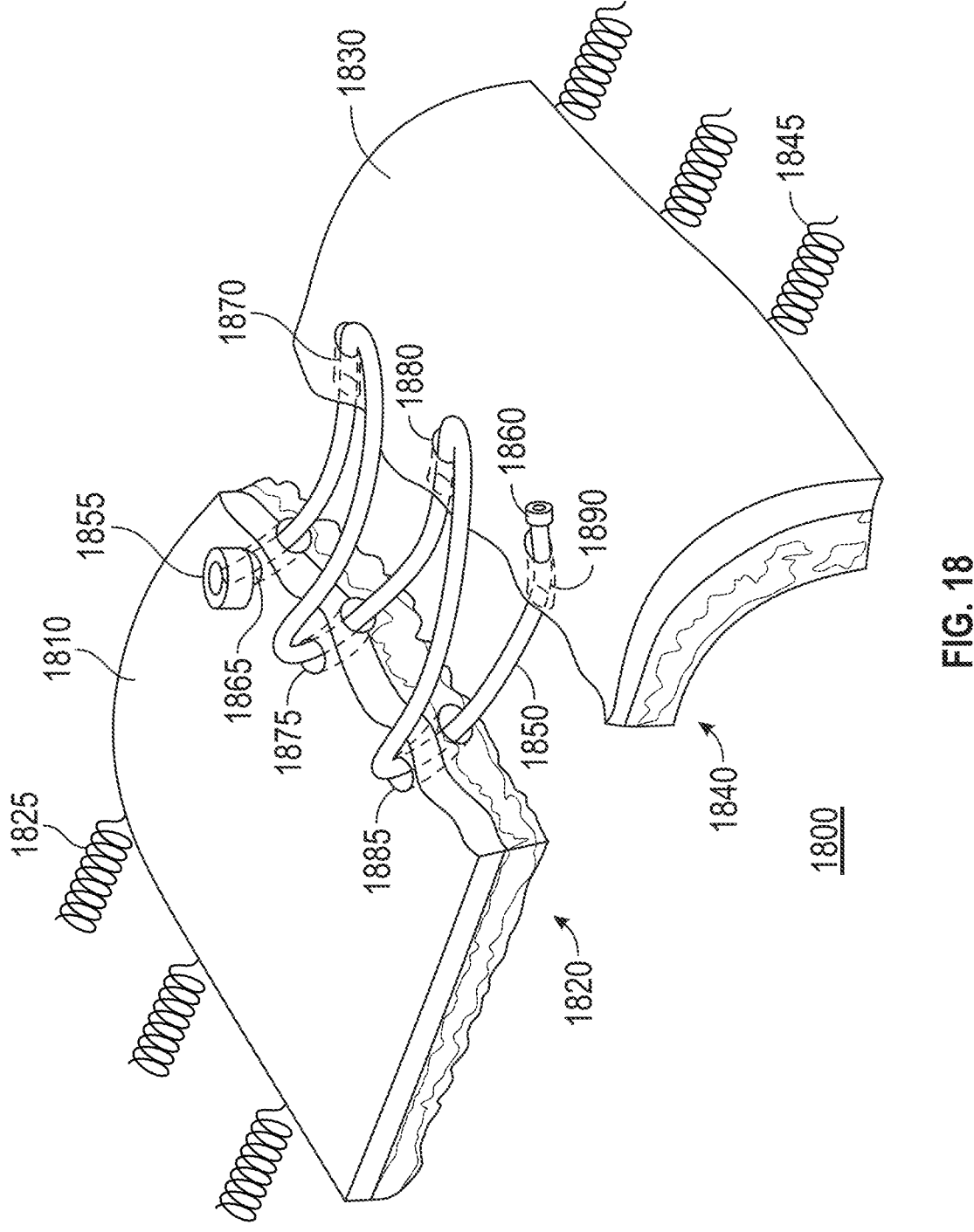

Referring now to FIGS. 16, 17 and 18, different examples of sutures of various orientations and suture types are shown. In FIG. 16, suture example 1600 for two layers 1610 and 1620 is shown; these may be Epidermis 1610 and Camper fascia 1620, for example. In this example, there are two vertically oriented prefabricated pathways 1630 that connected layers 1610 and 1620 while horizontally orientated prefabricated pathway 1660 resides in layer 1620. In the enlargement, blunted needle 1640 is inserted into top hole 1635 in a downward motion to pull suture thread 1650 down through prefabricated pathway 1630. The ability to come vertically from the superior surface (Epidermis layer 1610) allows a simple interrupted suture technique to be practiced. Blunted needle 1670 is inserted into the right opening 1665 of prefabricated pathway 1660 and path towards left exit hole 1665 to pull suture thread 1680 horizontally from right to left through pathway 1660. In this stitch, the ability to come horizontally through the precannulated, prefabricated pathway 1660 is helpful for practicing a subcutaneous running suture technique.

Example 1700 of FIG. 17 illustrates an example of a running subcutaneous suture technique. Two layers 1710 and 1720 on the left are separated from layers 1730 and 1740 on the right; the space between them defines an incision to be closed. As in FIG. 16, the top layer 1710, 1730 is the Epidermis skin layer while subcutaneous adipose tissue (fat) is the layer 1720, 1740 below. The left and right sides are attached to the opposing sides of the frame or housing (not shown) via one or more tensioning mechanisms, springs 1725 and 1745, respectively. A number of prefabricated, generally horizontally oriented pathways 1760, 1765, 1770 and 1775 are used by a running suture technique to draw the left and right sides towards each other, thereby closing up the incision (space) between the two sides.

Blunted needle coupled to suture thread 1750 is inserted first into pathway 1760 and pulled through. Next the needle is inserted into and pulled through pathway 1765 and is next threaded through pathway 1770 and finally through pathway 1775. Pulling the blunted needle with attached suture thread through these pathways will have the effect of pulling the two sides towards each other. The needle and thread may be pulled until anchor 1755 stops at the entry hole of pathway 1760.

In FIG. 18, an example 1800 of how the safety suture kit can be used to practice another suture technique is illustrated. Again, top layer 1810, 1830 may be Epidermis while the next layer down 1820, 1840 may be subcutaneous adipose tissue (fat); both sides are attached to the kit frame or housing (not shown) via spring tensioning mechanisms 1825, 1845, respectively. Threading suture thread 1850 with attached anchor 1855 sequentially through vertically orientated prefabricated pathways 1865, 1870, 1875, 1880, 1885, 1890, in that order, pulls the left and right sides together. In this example, an articulated blunted needle was used. The needle attachment point 1860 separates from the blunted needle and can screw into the anchor 1855 for more novice users.

The safety suture kit's premade or prefabricated cannulated pathways with prefabricated holes reinforce the utilization of proper surgical technique when rotating the blunted suture "needle" and needle driver through the tissue. This supports development of the fine motor skills and manual dexterity needed in surgical subspecialties like Otolaryngology. The prefabricated design embedded in the multilayer tissue design enhances the durability of the tissue and reusability of the kit.

The multilayer design provides education while maintaining anatomical realism. Optional diagrams on the kit teach the user about the seven tissue layers that are transversed during laparotomies, for instance. This kit design has the added benefit of providing the user with guided training in performing deep layer suturing. A clear window on the frame of the kit allows a view of the closure of the tissue for real time feedback.

The present safety suture simulation device and kit improves various aspects of previous training suture kits. Compared to other suture training kits, the present design puts safety at the forefront. This safety suture kit is a safety suture simulation kit that drastically reduces the potential for sharp injury by doing away with the scalpel, the metal point of the needle, and the suture scissors and replacing these tools with a blunted needle and safety shears similar to the kind used in many safety cautious pre-k and kindergarten classrooms. The blunted needle completely eliminates the chances of accidental sticks. The kit has a safer design in which a scalpel is not needed because the incisions and holes come prefabricated. The safety trio described herein—the absent scalpel, blunted needle, and safety scissors-theoretically make the equipment safe for users of all ages, including the youngest user, aged 4 and up.

Moreover, the present disclosure addresses the durability of the practice suture pad for previous training suture kits. The safety suture kit with prefabricated cannulated pathways within the tissue layers and prefabricated holes of the pathways removes the user's ability to free-hand the suturing process, forcing the user to utilize the proper mechanism of rotating the needle driver allowing the needle to transverse the tissue correctly without tearing the tissue. With practice, the user's fine motor skills and manual dexterity will improve and become second nature even before entering the O.R. for the first time.

The safety suture kit's design and construction may include low-tech, modified mannequin materials, with other contemplated designs including alternate materials to reduce cost, production time, and weight of the kit. A combination of 3D printing, wood, metals, silicon, and other synthetic skin substitutes, for example, may be used to reduce cost and production time. Sketched blueprints may be converted into a working one-layer prototype built from modular pieces. For example, a one layer Lego® model may be converted to a more aesthetically pleasing design using 3D printing. A final product may come with a pamphlet/book curriculum and short videos covering anatomy and suture topics for users of all ages.

Use of the safety suture kit described herein helps users accomplish a number of important learning objectives and skills, including:

Hone dexterity and familiarization with surgical techniques: Users will understand how to hold and utilize the needle drive and pickups properly when suturing tissue.

Gain knowledge about gross human anatomy: Users will learn about the human anatomy and that it is more than skin deep.

Build an understanding of types of wounds and wound closure techniques: Users will be able to close the wound and recall the closure techniques: subcutaneous, vertical/horizontal mattress, or deep dermal sutures.

Practice suturing in a safe environment: Users will be able to practice, experiment with minor supervision, and without fear of injury to themselves or others.

In view of the description and the accompanying drawings that accompany and form part of the specification, it can be seen that at least the following are novel, nonobvious and advantageous features and characteristics of the safety suture kit:

Prefabricated Cannulated Holes increase durability and reusability and reinforce the development of mechanics needed in most surgical procedures.

Individual Tensioning Mechanisms such as layered Spring-loaded Tension Springs (instead of rubber bands) increase durability and ease of replacement or adjustment of tension based on user experience and strength. Spring loading may be more durable and provide better tension/stability than rubber bands, which can tend to break, for example. The tension of different springs may be adjustable.

Individual layers allow semi-individual/semi-independent movement of the layers above and below the current working area. Wheels, slats or other movement mechanisms can be used to move layers of muscle over the layer below it. Muscle may rolls on top of the bottom of the kit while scarpa's fascia rolls over top of muscle, for example.

Blunted fabricated needles mean no self-sticks by users due to sharp, penetrating needle ends. The blunted needle size enhances the development of dexterity as the user learns to drive the needle through prefabricated holes and transverses the cannula to exit the tissue. The size of the needle will also help reduce the likelihood of being a choking hazard for our young users or household family members.

Needle Anchor allows even users who are unable to make a knot to perform running suture techniques.

Embodiments of the present disclosure advantageously provide a safety suture kit and methodology for using. The embodiments described above and summarized below are combinable.

In one embodiment of a safety suture kit, the kit includes layers that are moveable and operable to be tensioned to a frame of the safety suture kit, the layers representative of tissue layers; prefabricated incisions formed in the plurality of layers; prefabricated pathways and holes associated therewith formed in the layers, with each prefabricated pathway coupled to a prefabricated incision of the one or more prefabricated incisions in the layers and having one or more holes therethrough. Responsive to a suture thread pushed under tension through holes of prefabricated pathways coupled to the prefabricated incision, the layers move towards a closed position of the prefabricated incision.

In another embodiment of the kit, the layers are independently moveable with respect to each other.

In another embodiment of the kit, one or more layers are coupled to one or more movement mechanisms operable to provide independent movement of the layers of the safety suture kit.

In another embodiment of the kit, the movement mechanisms include one or more of wheels and slats attached to the layers to provide independent movement of the layers with respect to other layers.

In another embodiment of the kit, the safety suture kit further including the frame, where the layers are coupled to tensioning mechanisms operable to tension the layers to the frame.

In another embodiment of the kit, the tensioning mechanisms are coupled to side walls and a bottom surface of the frame.

In another embodiment of the kit, the tensioning mechanisms are replaceable and removable springs or rubber bands.

In another embodiment of the kit, further including a window in the frame that permits a user to see the plurality of layers, the plurality of prefabricated pathways and associated holes, and the one or more fabricated incisions.

In another embodiment of the kit, the window provides a sagittal view of the layers, the prefabricated pathways and associated holes, and the fabricated incisions.

In another embodiment of the kit, the window is formed in a front wall of the frame.

In another embodiment of the kit, the prefabricated pathways are cannulated pathways and the prefabricated holes are cannulated holes.

In another embodiment of the kit, further including a blunted suture needle suitable for guiding a suture thread through the prefabricated pathways via the holes therethrough.

In another embodiment of the kit, the blunted needle having a point of articulation to couple to suture thread.

In another embodiment of the kit, the point of articulation is threaded and operable to couple to a screw-threaded connection of the suture thread.

In another embodiment of the kit, the threaded anchor operable to couple to the screw-threaded connection of the suture thread.

In another embodiment of the kit, further including an anchor operable to be coupled to the suture thread at an end of the suture thread distal the blunted suture needle.

In another embodiment of the kit, one or more layers having one or more slates that move semi-independently in a first progression during movement in a first direction and in a second progression during movement in a second direction that is opposite the first direction.

In another embodiment of the kit, adjacent slates are coupled to each other by a corresponding latch.

In another embodiment of the kit, layers include a layer scaffolding having a plurality of openings configured to accommodate the prefabricated pathways, with simulated tissue formed over the layer scaffolding.

In another embodiment of the kit, the prefabricated pathways are oriented horizontally or vertically with regard to the openings of the layer scaffolding of one or more of the layers.

While implementations of the disclosure are susceptible to embodiment in many different forms, there is shown in the drawings and will herein be described in detail specific embodiments, with the understanding that the present disclosure is to be considered as an example of the principles of the disclosure and not intended to limit the disclosure to the specific embodiments shown and described. In the description above, like reference numerals may be used to describe the same, similar or corresponding parts in the several views of the drawings.

In this document, relational terms such as first and second, top and bottom, and the like may be used solely to distinguish one entity or action from another entity or action without necessarily requiring or implying any actual such relationship or order between such entities or actions. The terms "comprises," "comprising," "includes," "including," "has," "having," or any other variations thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Reference throughout this document to "one embodiment," "certain embodiments," "an embodiment," "implementation(s)," "aspect(s)," or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C." An exception to this definition will occur only when a combination of elements, functions, steps or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," "for example," or the like) provided herein, is intended merely to better illuminate the embodiments and does not pose a limitation on the scope of the embodiments. No language in the specification should be construed as indicating any unclaimed element as essential to the practice of the embodiments.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

In the following description, it is understood that terms such as "first," "second," "top," "bottom," "up," "down," "above," "below," and the like, are words of convenience and are not to be construed as limiting terms. Also, the terms apparatus, device, system, etc. may be used interchangeably in this text.

The many features and advantages of the disclosure are apparent from the detailed specification, and, thus, it is intended by the appended claims to cover all such features and advantages of the disclosure which fall within the scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

What is claimed is:

1. A safety suture kit, comprising:
a plurality of layers that are moveable and operable to be tensioned to a frame of the safety suture kit, the plurality of layers representative of tissue layers;
one or more prefabricated incisions formed in the plurality of layers;
a plurality of prefabricated pathways and a plurality of holes associated therewith formed in the plurality of layers, each prefabricated pathway coupled to a prefabricated incision of the one or more prefabricated incisions in the plurality of layers and having one or more holes therethrough,
where responsive to a suture thread pushed under tension through holes of one or more of the prefabricated pathways coupled to the prefabricated incision, one or more of the layers move towards a closed position of the prefabricated incision; where one or more layers of the plurality of layers comprise one or more slates that move semi-independently in a first progression during movement in a first direction and in a second progression during movement in a second direction that is opposite the first direction.

2. The safety suture kit of claim 1, where the plurality of layers are independently moveable with respect to each other.

3. The safety suture kit of claim 1, where one or more layers of the plurality of layers are coupled to one or more movement mechanisms operable to provide independent movement of the one or more layers of the safety suture kit.

4. The safety suture kit of claim 3, where the one or more movement mechanisms include one or more of wheels and slats attached to one or more layers and provide independent movement of the one or more layers with respect to other layers of the plurality of layers.

5. The safety suture kit of claim 1, further comprising the frame, where one or more of the plurality of layers are coupled to one or more tensioning mechanisms operable to tension the one or more layers to the frame of the safety suture kit.

6. The safety suture kit of claim 5, where the one or more tensioning mechanisms are coupled to one or more of side walls and a bottom surface of the frame.

7. The safety suture kit of claim 5, where the one or more tensioning mechanisms are one or more of replaceable and removable springs and rubber bands.

8. The safety suture kit of claim 5, further comprising:
a window in the frame that permits a user to see the plurality of layers, the plurality of prefabricated pathways and associated holes, and the one or more fabricated incisions.

9. The safety suture kit of claim 8, where the window provides a sagittal view of one or more of the plurality of layers, the plurality of prefabricated pathways and associated holes, and the one or more fabricated incisions.

10. The safety suture kits of claim 9, where the window is formed in a front wall of the frame.

11. The safety suture kit of claim 1, where the plurality of prefabricated pathways are cannulated pathways and the plurality of associated prefabricated holes are cannulated holes.

12. The safety suture kit of claim 1, further comprising:
a blunted suture needle suitable for guiding a suture thread through one or more of the plurality of prefabricated pathways via the one or more holes therethrough.

13. The safety suture kit of claim 12, the blunted needle having a point of articulation operable to couple to the suture thread.

14. The safety suture kit of claim 13, where the point of articulation is threaded and operable to couple to a screw-threaded connection of the suture thread.

15. The safety suture kit of claim 14, further comprising a threaded anchor operable to couple to the screw-threaded connection of the suture thread.

16. The safety suture kit of claim 12, further comprising:
an anchor operable to be coupled to the suture thread at an end of the suture thread distal the blunted suture needle.

17. The safety suture kit of claim 1, where adjacent ones of the one or more slates are coupled to each other by a corresponding latch.

18. The safety suture kit of claim 1, where one or more layers of the plurality of layers include a layer scaffolding having a plurality of openings configured to accommodate the plurality of prefabricated pathways, with simulated tissue formed over the layer scaffolding.

19. The safety suture kit of claim 18, where the plurality of prefabricated pathways are oriented horizontally or vertically with regard to the plurality of openings of the layer scaffolding of one or more layers of the plurality of layers.

* * * * *